US009326663B2

(12) United States Patent
Viola et al.

(10) Patent No.: US 9,326,663 B2
(45) Date of Patent: May 3, 2016

(54) ENDOLUMINAL CRAWLER (75) Inventors: Frank J. Viola, Sandy Hook, CT (US); James M. Power, Madison, CT (US)

(73) Assignee: Covidien LP, Mansfield, MA (US)

( * ) Notice: Subject to any disclaimer, the term of this patent is extended or adjusted under 35 U.S.C. 154(b) by 1091 days.

(21) Appl. No.: 13/108,344

(22) Filed: May 16, 2011

(65) Prior Publication Data
US 2011/0313249 A1  Dec. 22, 2011

Related U.S. Application Data (60) Provisional application No. 61/355,638, filed on Jun. 17, 2010.

(51) Int. Cl.
*A61B 1/00* (2006.01)
*G02B 23/24* (2006.01)
*A61B 1/04* (2006.01)
*A61M 31/00* (2006.01)
*A61B 17/00* (2006.01)
*A61B 17/29* (2006.01)
*A61B 19/00* (2006.01)

(52) U.S. Cl.
CPC ........... *A61B 1/00156* (2013.01); *A61B 1/0016* (2013.01); *A61B 1/00101* (2013.01); *G02B 23/2476* (2013.01); *A61B 2017/00292* (2013.01); *A61B 2017/2908* (2013.01); *A61B 2019/2211* (2013.01); *A61B 2019/2219* (2013.01)

(58) Field of Classification Search
CPC ......... A61B 1/00156; A61B 1/04; A61B 1/31
USPC ............... 600/104, 114, 127–129; 356/241.1; 305/33, 116, 124, 126, 127, 194; 604/95.01–95.03
See application file for complete search history.

(56) References Cited

U.S. PATENT DOCUMENTS

| 4,249,536 A | 2/1981 | Vega |
| 4,717,381 A | 1/1988 | Papantonakos |
| 5,142,989 A | 9/1992 | Suzumori et al. |
| 5,398,670 A | 3/1995 | Ortiz et al. |
| 5,817,057 A | 10/1998 | Berenstein et al. |
| 5,878,783 A | 3/1999 | Smart |
| 5,919,128 A * | 7/1999 | Fitch .............................. 600/166 |
| 6,059,767 A | 5/2000 | Noriega |
| 6,332,865 B1 | 12/2001 | Borody et al. |
| 6,450,104 B1 | 9/2002 | Grant et al. |
| 6,517,477 B1 | 2/2003 | Wendlandt |

(Continued)

FOREIGN PATENT DOCUMENTS

| JP | 2005-253892 A | 9/2005 |
| JP | 2009-106431 A | 5/2009 |

OTHER PUBLICATIONS

European Examination Report for EP 11 250 595.3 dated Jan. 7, 2016.

*Primary Examiner* — Ryan Henderson
*Assistant Examiner* — Timothy J Neal (57) ABSTRACT An endoluminal crawler used in endoscopic procedures includes a body and an actuation unit. The body includes a tubular portion. The actuation unit includes an actuator providing a rotational output and a traction belt. The traction belt includes a traction portion and an engaging portion. The traction portion protrudes out of a slot defined in the tubular portion and the engaging portion operatively engages the actuator.

20 Claims, 7 Drawing Sheets

(56) References Cited

U.S. PATENT DOCUMENTS

| | | |
|---|---|---|
| 6,695,771 B2 | 2/2004 | Takada |
| 6,699,179 B2 | 3/2004 | Wendlandt |
| 6,702,734 B2 | 3/2004 | Kim et al. |
| 6,866,626 B2 | 3/2005 | Long et al. |
| 7,066,880 B2 | 6/2006 | Wendlandt |
| 7,087,011 B2 | 8/2006 | Cabiri et al. |
| 7,172,552 B2 | 2/2007 | Wendlandt |
| 2002/0107478 A1 | 8/2002 | Wendlandt |
| 2002/0173700 A1 | 11/2002 | Kim et al. |
| 2003/0093031 A1 | 5/2003 | Long et al. |
| 2005/0272976 A1 | 12/2005 | Tanaka et al. |
| 2006/0089533 A1* | 4/2006 | Ziegler et al. .............. 600/114 |
| 2007/0083081 A1 | 4/2007 | Schlagenhauf et al. |
| 2007/0167685 A1 | 7/2007 | Watanabe |
| 2008/0097292 A1 | 4/2008 | Cabiri et al. |
| 2008/0103440 A1 | 5/2008 | Ferren et al. |
| 2009/0024085 A1 | 1/2009 | To et al. |
| 2009/0028957 A1 | 1/2009 | Daniloff |
| 2009/0082722 A1 | 3/2009 | Munger et al. |
| 2009/0102281 A1* | 4/2009 | Diekevers et al. ............ 305/104 |
| 2011/0054257 A1 | 3/2011 | Stopek |

* cited by examiner

FIG_2
PRIOR ART

FIG_1
PRIOR ART

FIG_10

ENDOLUMINAL CRAWLER

This application claims priority from provisional application Ser. No. 61/355,638, filed Jun. 17, 2010, the entire contents of which are incorporated herein by reference.

BACKGROUND

1. Technical Field

The present disclosure relates generally to an endoscopic apparatus and, more particularly, to a self-propelled endoluminal device that moves in a tubular organ.

2. Background of Related Art

A typical endoscope includes a flexible tube that is inserted through the gastrointestinal tract of a patient starting from the rectum or from the esophagus. The tip of the endoscope that is introduced in the gastrointestinal tract can be outfitted with several devices, most notably a light source and a camera, so that a user of the endoscope can observe the interior of the gastrointestinal tract and maneuver the endoscope to the proper position.

Once the endoscope is placed at the desired location in the gastrointestinal tract, surgical tools may be inserted through a working channel defined in the endoscope. As such, the surgical tools inserted in the endoscope will also easily reach the desired location.

The conventional method requires a highly skilled endoscopist to steer and push the endoscope through the gastrointestinal tract. However, even the highly skilled endoscopist oftentimes faces the difficulty of having to maneuver the long flexible tube through a narrow cavity, while steering the distal end of the flexible tube inside the body cavity. This can create an inherently unstable condition, which may result in excessive extension or dilation of the tubular organ. The excessive extension or dilation of the tubular organ causes pain and discomfort in patients, and can increase the risk of puncturing of the wall of the tubular organ which can cause infection or peritonitis.

SUMMARY

In accordance with one aspect of the present disclosure, there is provided a self-propelled endoluminal device including a body and an actuation unit disposed within the body. The body includes a tubular portion defining at least one slot. The actuation unit includes an actuator providing a rotational output and a traction belt including a traction portion and an engaging portion. The traction portion at least partially protrudes out of the slot and the engaging portion operatively engages the actuator.

Preferably, a tapered portion extends longitudinally from the tubular portion. The tapered body portion can include a flexible material configured to adapt to the shape of a tubular organ.

In some embodiments, a roller rotatably supports the traction belt in the body and the traction belt is continuously looped such that the rotational output of the actuator provides continuous rotation of the traction belt within the slot.

In some embodiments, the actuation unit may include a worm gear defining a longitudinal axis operatively coupled to the actuator and engaging the engaging portion of the traction belt. The continuously looped traction belt can extend along the length of the worm gear. The worm gear in some embodiments may define a working channel therein, and the working channel can extend along the length of the worm gear. In some embodiments, a distal end portion of the body may define an aperture in communication with the working channel. The aperture can be configured to receive surgical tools therethrough.

In some embodiments, the traction belt includes a plurality of substantially transverse grooves configured to engage teeth of a gear, e.g. a worm gear. Alternatively, the traction belt may include a plurality of ribs configured to engage teeth of a gear such as a worm gear.

In alternate embodiments, the actuation unit may include a pinion gear operatively coupled to the actuator and engaging the engaging portion of the traction belt such that the rotational output of the actuator rotates the continuously looped traction belt.

In some embodiments, the body may include a viewing window radially surrounding the aperture. The viewing window can be made of transparent material.

The device may further include an internal power source to supply power to the actuator providing the rotational output. The device may further include a light source. The light source can be powered by the internal power source.

In accordance with another aspect, the present disclosure provides an endoluminal device comprising a body and a traction member disposed within the body, the body having a slot formed therein to provide an opening for the traction member to contact an inner surface of a body lumen. The traction member has a traction surface engageable with the body lumen inner surface, the traction member being movable to advance the endoluminal device along the body lumen.

The traction member may include a traction belt maintained in a continuous loop movable in a direction along a longitudinal axis of the device. A gear mechanism can be provided for moving the traction belt. In some embodiments, the length of the belt can exceed the length of the slot.

In accordance with another aspect of the present disclosure, there is provided an endoscope including a housing, a flexible tube longitudinally extending from the housing, and an endoluminal device attached to the flexible tube. The endoluminal device includes a body and an actuation unit disposed within the body. The body includes a tubular portion defining at least one slot, preferably a longitudinal slot. The actuation unit includes an actuator providing a rotational output and a traction belt including a traction portion and an engaging portion. The traction portion partially protrudes out of the slot and the engaging portion operatively engages the actuator.

In some embodiments, a roller rotatably supports the traction belt in the body. The traction belt is preferably continuously looped such that the rotational output of the actuator provides continuous rotation of the traction belt at least partially within the at least one longitudinal slot. At least one roller can be provided to rotatably support the traction belt in the body.

In some embodiments, the housing defines an aperture in communication with the body to receive a surgical tool therethrough. The body can define an opening at a distal portion thereof in communication with the aperture for receiving therethrough the surgical tool.

In some embodiments, the actuation unit further includes a worm gear operatively coupled to the actuator and engaging the engaging portion of the traction belt. In some embodiments, the worm gear defines a working channel therein extending along a length of the worm gear.

In alternate embodiments, the actuation unit further includes at least one pinion gear, the at least one pinion gear being operatively engaged to the actuator and engaging the engaging portion of the traction belt such that the rotational output of the actuator rotates the continuously looped traction belt.

In some embodiments, the distal end portion of the body includes a viewing window, the viewing window radially surrounding the opening and further comprising a camera in the body adjacent the viewing window.

In some embodiments, the tapered portion of the body includes a flexible material, and is configured to adapt to the shape of a tubular member. The tapered portion can extend longitudinally from the tubular portion.

The endoluminal device can in some embodiments be releasably attached to the flexible tube.

BRIEF DESCRIPTION OF THE DRAWINGS

The above and other objects and features of the present disclosure will become apparent from the following description of embodiments given in conjunction with the accompanying drawings, in which.

DETAILED DESCRIPTION

Various embodiments of the presently disclosed endoluminal device will now be described in detail with reference to the drawings, wherein like reference numerals identify similar or identical elements. In the drawings and in the description that follows, the term "proximal," will refer to the end of a device or system that is closer to the operator, while the term "distal" will refer to the end of the device or system that is further from the operator.

Figures 1, 2:
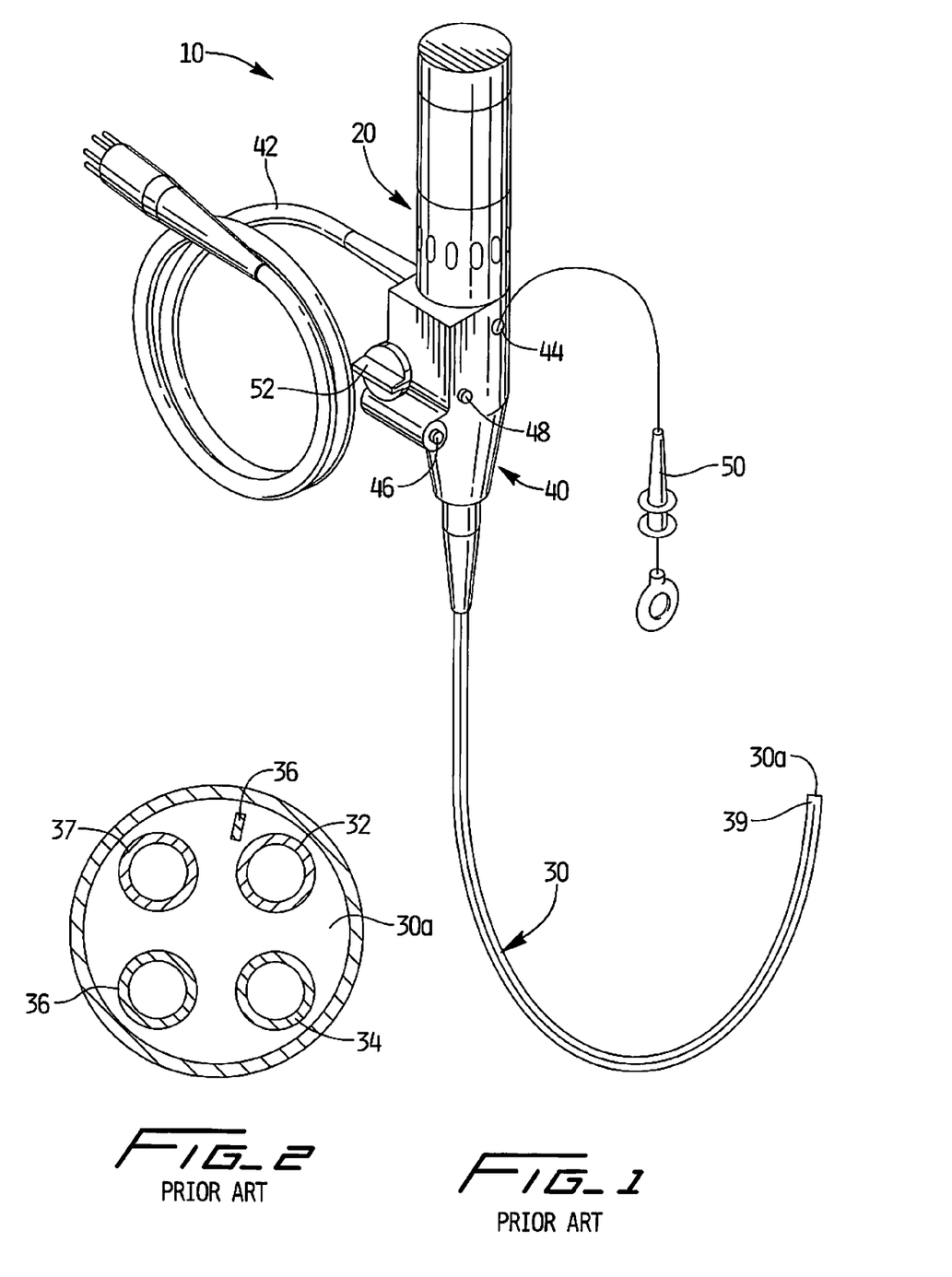
FIG. 1 is a perspective view of a prior art endoscope.
FIG. 2 is a cross-sectional view of a distal end of an insertion tube of the endoscope of FIG. 1.

A prior art endoscope is illustrated in FIG. 1 and is designated by reference numeral 10. Endoscope 10 includes an endoscope housing 20 and a flexible insertion tube 30 extending distally from housing 20. As best shown in FIG. 2, insertion tube 30 defines therein a viewing channel 32, a light source channel 34, a suction channel 36, a tool channel 37, and water/air supply channel 38.

Viewing channel 32 may include a viewing window at a distal end thereof. A camera or fiber optic bundle is inserted through viewing channel 32 to capture images of a tubular organ through the viewing window. The captured images are transmitted to an operation unit 40 which transfers the images to an external display terminal (not shown) via a universal cord 42. In addition, a light source (not shown) is provided through light source channel 34 to aid the user in viewing the surgical site and maneuvering distal section 30a. Air or water may be supplied to the surgical site by a nozzle provided at a distal end of water/air supply channel 38. A button 46 on operation unit 40 may be operated to turn on or off the air or water supply. The air or water supplied by the nozzle is suctioned through an opening provided at a distal end of suction channel 36. The suction can be performed by an operation of a suction control button 48. The fluid suctioned through opening 36 is discharged out of the patient's body. Tool channel 37 is in communication with insertion opening 44 defined in operation unit 40 such that upon positioning distal end 30a of insertion tube 30 at the surgical site of interest, surgical tools, e.g., forceps 50, may be inserted through insertion opening 44 and be directed to the surgical site through tool channel 37. A bending section 39 of flexible insertion tube 30 at the distal portion may be remotely manipulated in multi-directions through the use of control knob 52 on operation unit 40.

Figure 3:
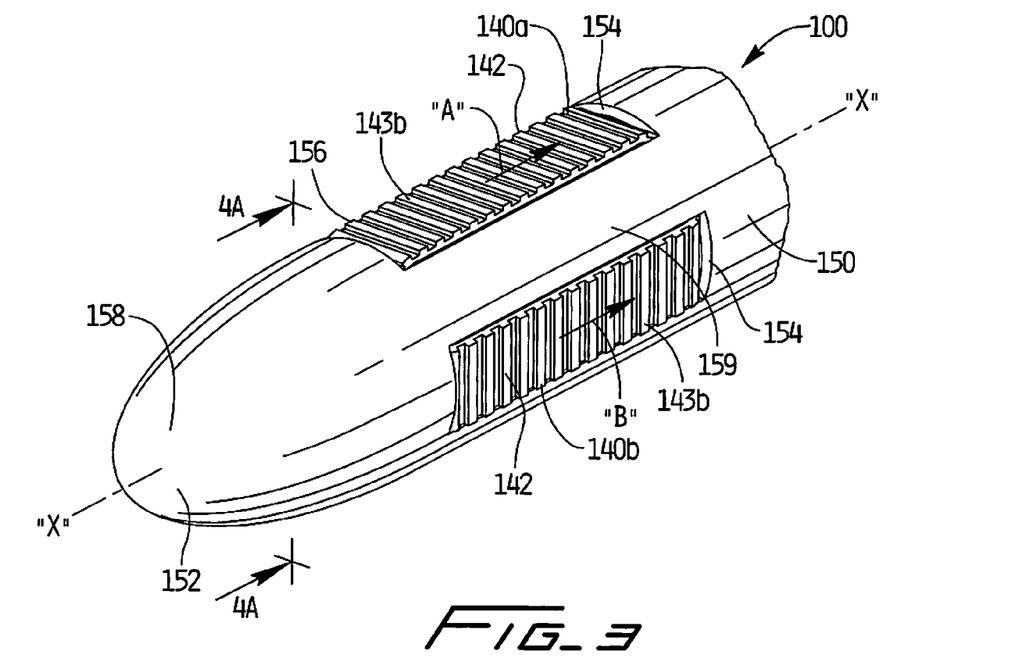
FIG. 3 is a perspective view of an endoluminal crawler in accordance with an embodiment of the present disclosure.
Figure 4:
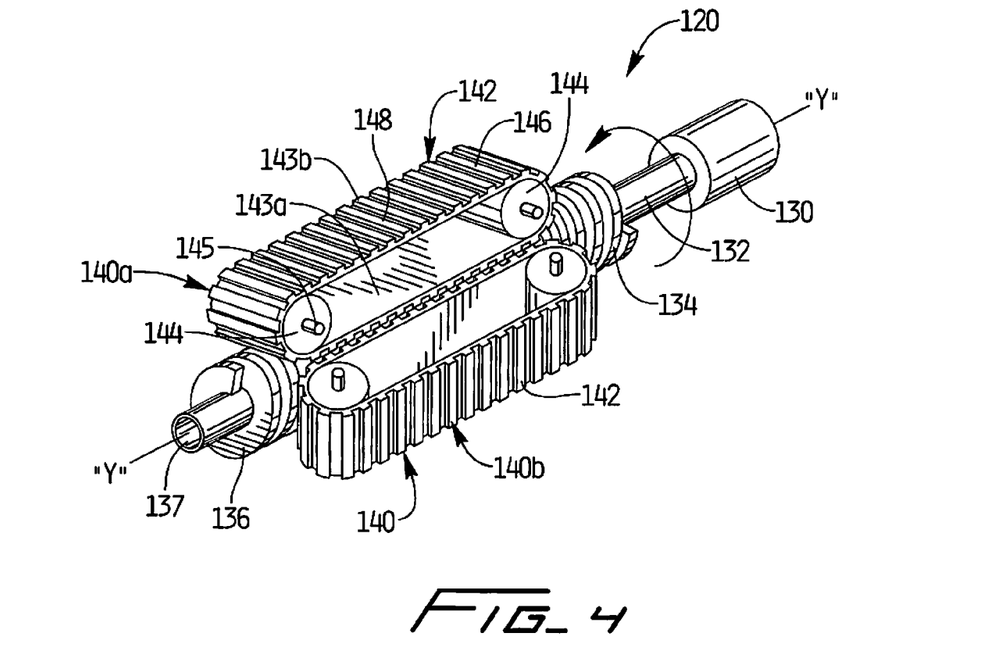
FIG. 4 is a top perspective view of an actuation unit of the endoluminal crawler of FIG. 3.
Figure 10:
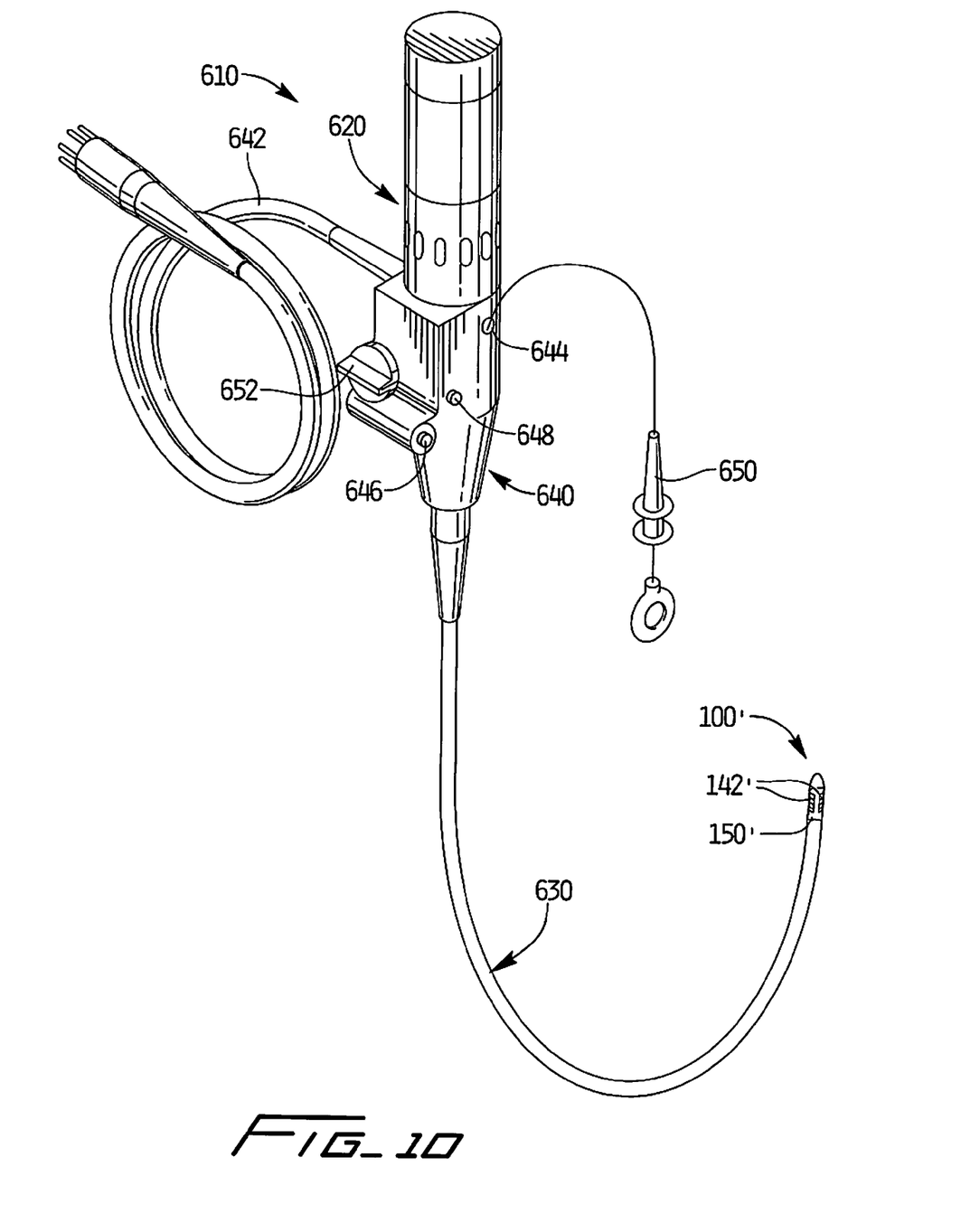
FIG. 10 is a perspective view of an endoluminal crawled mounted on an endoscope tube.

Referring now to FIGS. 3 and 4, an embodiment of the present disclosure is shown generally as an endoluminal device 100. Endoluminal device 100 is a crawler device which includes an outer body 150 and an actuation unit 120 positioned within outer body 150. While the size of outer body 150 may be tailored to meet the specific needs of the procedure being performed, outer body 150 in most applications is dimensioned so that outer body 150 is large enough to accommodate actuation unit 120 therein, but small enough to fit within the smallest expected dimension of the tubular organ. Endoluminal crawler 100 may be employed as an independent module, or alternatively as an attachment to a conventional endoscope e.g., at a distal end portion of the insertion tube, to facilitate navigation of the insertion tube through a tubular organ. An example of endoluminal device mounted to an endoscope is shown in FIG. 10. As an independent module, surgical tools are attached to endoluminal crawler 100 which guides the surgical tools to a surgical site of interest to carry out, for example, removal of polyps, irrigation, and suction. A camera or illuminator can be attached to the front (distal) portion of the crawler for visualization as advanced. Endoluminal crawler 100 navigates through the labyrinth of the gastrointestinal tract or other body lumens with less difficulty, as compared to manual insertion of the flexible insertion tube 30 of the prior art endoscope 10 through the tubular organ.

Outer body 150 of endoluminal crawler 100 includes a generally tubular portion 156 and a tapered distal portion 158 with respect to a longitudinal axis "X-X" to facilitate navigation through the tubular organ. As such, body 150 has a streamlined torpedo-like shape. Tapered portion 158 distally extending from tubular portion 156 may be integrally formed with tubular portion 156. Tapered portion 158 may alternatively be attached to tubular portion 156 and may include a flexible or resilient material for navigating through the tubular organs. A tapered portion, e.g. torpedo-like shape, can also be formed at the opposing end in each of the embodiments disclosed herein to facilitate movement in the reverse direction. Tubular portion 156 of outer body 150 defines a plurality of spaced apart longitudinal slots 154 in communication with an interior of body 150. The longitudinal slots 154 are shown longitudinally aligned but alternatively one or more of the slots can be longitudinally offset. Slots 154 are preferably uniformly spaced around the radial perimeter of outer body 150, though non-uniform spacing is also contemplated. Each longitudinal slot 154 accommodates a traction belt 142 of actuation unit 120 which partially protrudes through longitudinal slot 154 to provide traction against an interior wall of the tubular organ. Each traction belt 142 is preferably continuously looped, as will be discussed in greater detail below. Outer body 150 may be made of or coated with a material providing reduced friction with the interior wall of the tubular organ.

Figure 5:
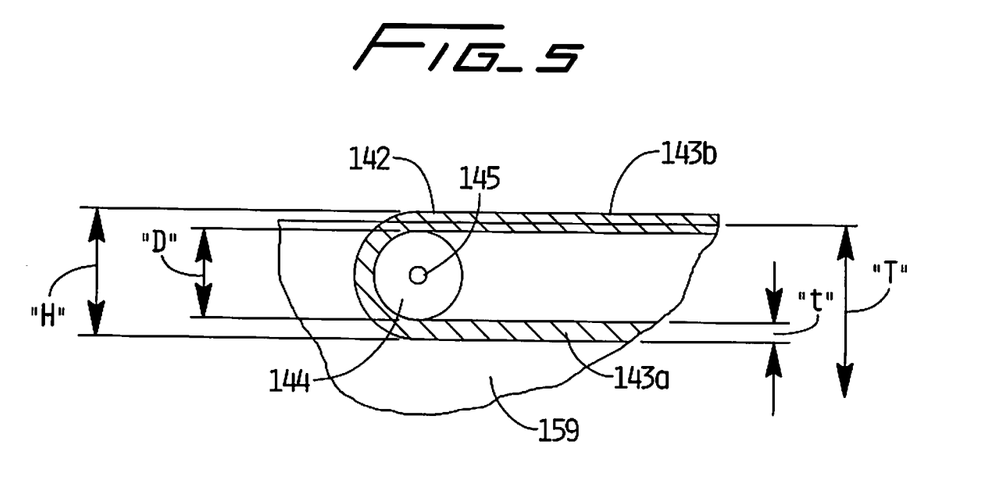
FIG. 5 is a partial longitudinal cross-sectional view of a longitudinal slot defined in the endoluminal crawler of FIG. 3.

With particular reference to FIG. 4, actuation unit 120 is illustrated. Actuation unit 120 includes an actuation device 130, e.g., a motor, a drive shaft 132, a worm gear 134, and a traction unit 140. Actuation device 130 is operatively coupled to drive shaft 132 defining a longitudinal axis "Y-Y." Worm gear 134 is mounted on drive shaft 132 such that when actuation device 130 rotates drive shaft 132, worm gear 134 is concomitantly rotated therewith about longitudinal axis "Y-Y." Drive shaft 132 is preferably concentrically mounted with body 150 such that rotation of worm gear 134 moves traction units 140*a*, 140*b* which are arranged around the radial perimeter of the interior wall of tubular portion 156. Traction units 140*a*, 140*b* each include traction belt 142 and a set of rollers 144. Only one unit, i.e. unit 140*a*, is labeled in FIG. 4 for clarity. Each traction belt 142 provides a continuous loop and is supported on the interior wall of body 150 by the set of rollers 144. In particular, each roller 144 is rotatably supported by a support pin 145. Ends of each support pin 145 are securely attached to an internal side of a respective side wall 159, defining longitudinal slot 154 of body 150, as best seen in FIG. 5. Alternatively, the support pin can be rotatable with roller 144, and either a separate unit or formed integrally therewith.

At least one roller 144 is supported on the interior wall of body 150 adjacent a proximal portion of worm gear 134 and another roller 144 is supported on the interior wall of body 150 adjacent a distal end portion 136 of worm gear 134 such that traction belts 142 extend substantially along the length of worm gear 134. The spacing of rollers 144 and the length of traction belts 142 are chosen to provide proper tension in traction belts 142 when rotated in a continuous loop.

Figure 4A:
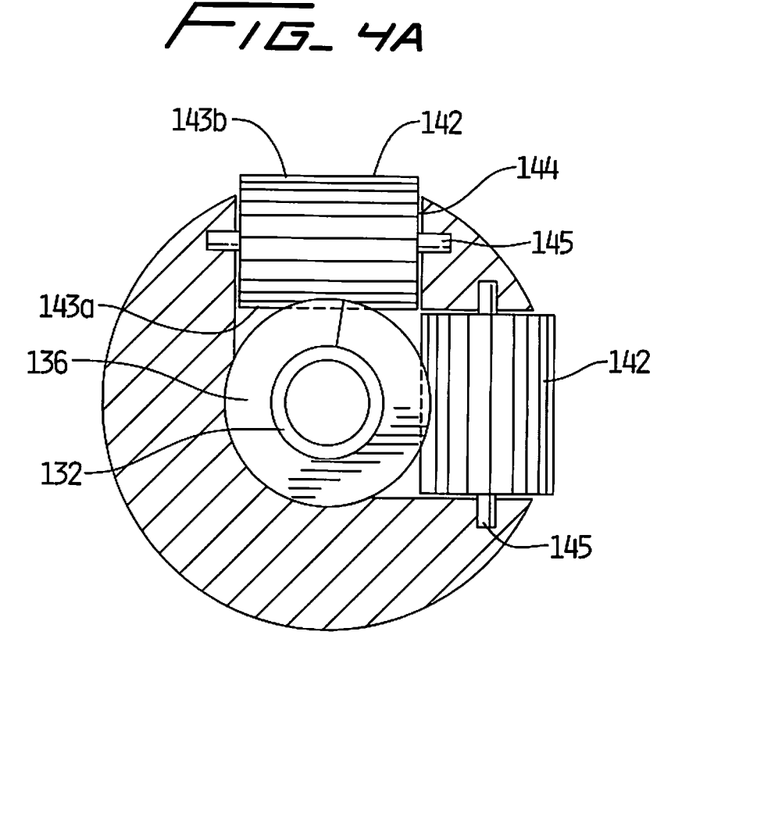
FIG. 4A is a cross-sectional view taken along lines 4A-4A of FIG. 3.

Each traction belt 142 includes treads 146 defining a plurality of substantially transverse grooves 148. The substantially transverse grooves 146 are illustratively uniformly arranged along the length of traction belt 142 and illustrated along a central region. The substantially transverse grooves 148 are configured to operatively engage and mesh with worm gear 134. The grooves are preferably slightly offset from 90° angles with respect to the longitudinal axis of the unit 120 but can also be at other angles. Rotation of worm gear 134 about longitudinal axis "Y-Y" rotates continuously looped traction belt 142. The continuously looped traction belt 142, as viewed in the position of FIGS. 4A and 4B, has an engaging portion 143*a* that engages worm gear 134 and a traction portion 143*b* protruding out of longitudinal slot 154 defined in outer body 150 and providing traction against the interior wall of the tubular organ. Because traction belt 142 is continuously looped, engaging portion 143*a* and traction portion 143*b* move in opposite directions when worm gear 134 rotates about longitudinal axis "Y-Y", and upon sufficient looping movement, engaging portion 143*a* becomes the tissue traction portion and traction portion 143*b* becomes the gear engaging portion. Change in the direction of travel for endoluminal crawler 100 can be achieved by simply changing the direction of rotation of worm gear 134 and the drive shaft 132. While traction belt 142 of FIG. 4 has treads 146 adjacent the plurality of transverse grooves 148, treads 146 may provide a plurality of protruding teeth configured to mesh with teeth provided on worm gear 134, as in the treads 246 of the embodiment of FIGS. 6 and 7 discussed in greater detail below.

With continued reference to FIG. 4, actuation unit 120 employs two traction units 140*a*, 140*b*. A size or diameter of worm gear 134 may be varied to accommodate a greater number of traction units 140 that operatively engage worm gear 134 around the radial perimeter of worm gear 134. The plurality of traction units 140 may enhance propulsion of endoluminal crawler 100 through the tubular organ by providing greater points of traction against the interior wall of the tubular organ. Even though the plurality of traction units 140 may require a larger worm gear 134, e.g., one that has a diameter larger than a width of traction belt 142, to accommodate a plurality of traction units 140 around the radial perimeter of worm gear 134, it can be appreciated that by actuating the plurality of traction units 140 through a use of a single worm gear 134, the overall size of endoluminal crawler 100 may be minimized. Moreover, it is further contemplated that each traction unit 140 may partially extend along the length of worm gear 134 such that a greater number of traction units 140 are accommodated on worm gear 134. In particular, by placing traction units 140 offset from each other around the radial perimeter and along the longitudinal axis "Y-Y" of worm gear 134, various non-uniform traction points against the interior wall of the tubular organ can be obtained. Such arrangement may provide enhanced traction against the interior wall of the tubular organ, as the tubular organ may not provide uniform contact against traction portions 143*b* while endoluminal crawler 100 travels through the tubular organ.

Protrusion of traction portion 143*b* out of longitudinal slot 154 ensures proper traction against the interior wall of the tubular organ. As a way of example, each roller 144 may be rotatably secured to a respective longitudinal side wall 159 defining longitudinal slot 154, as shown in FIG. 5. Under such arrangement, an adequate amount of protrusion of traction portion 143*b* out of longitudinal slot 154 is achieved by dimensioning a height "H" of traction belt 142 wrapped around roller 144 to be greater than a thickness "T" of outer body 150 (i.e., outer diameter of body 150−inner diameter of body 150).

Referring back to FIG. 4, worm gear 134 or shaft 132 may define a longitudinally extending working channel 137. Working channel 137 can be utilized for passage of a camera, surgical tools and water. Working channel 137 may further be partitioned into several different channels to perform different functions as described. Such design may have a distal end portion 152 of outer body 150 that includes, for example; a viewing window for the camera and an aperture through which the surgical tools exit. In addition, distal end portion 152 of outer body 150 may further include an illumination device to aid the user in viewing the surgical site and maneuvering the endoluminal crawler 100.

Figure 4B:
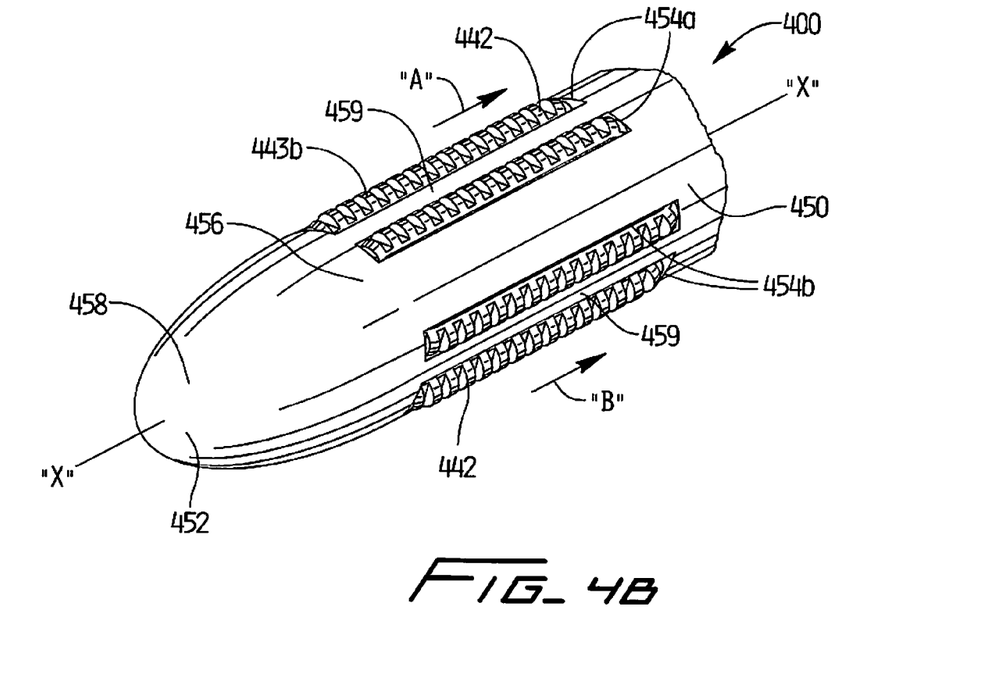
FIG. 4B is a perspective view of an alternate embodiment of the endoluminal crawler.
Figure 4C:
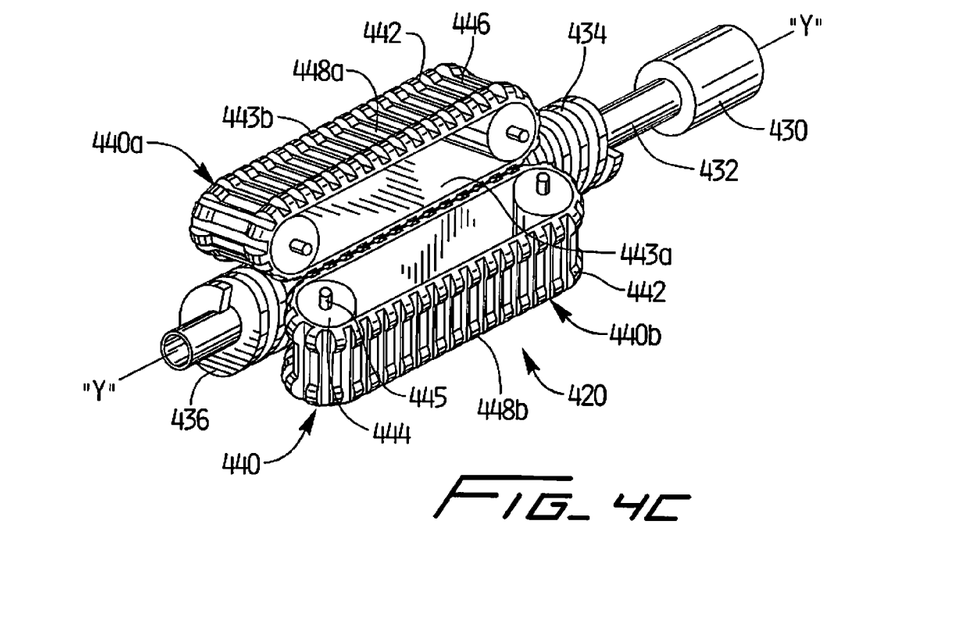
FIG. 4C is a top perspective view of an actuation unit of the endoluminal crawler of FIG. 4B.

In the alternate embodiment of FIGS. 4B and 4C, endoluminal device 400 has a body 450 with a tapered portion 458 extending from tubular portion 456. Endoluminal device differs from device 100 of FIG. 3 in that a portion of the traction belts are covered as described below. Slots 454*a*, 454*b* provide an opening for a respective traction belt 448*a*, 448*b*. Actuation unit 420 is illustrated in FIG. 4C. Endoluminal device 400 may be employed as an independent module or as an attachment to a conventional endoscopic apparatus.

Actuation unit 420 includes an actuation device 430, e.g., a motor, a drive shaft 432, a worm gear 434, and a traction unit 440. Actuation device 430 is operatively coupled to drive shaft 432 defining a longitudinal axis "Y-Y." Worm gear 434 is mounted on drive shaft 432 such that when actuation device 430 rotates drive shaft 432, worm gear 434 is concomitantly rotated therewith about longitudinal axis "Y-Y." Drive shaft 432 is preferably concentrically mounted with body 450 such that rotation of worm gear 434 moves traction units 440a, 440b which are arranged around the radial perimeter of the interior wall of tubular portion 456. Traction units 440a, 440b each include traction belt 442 and a set of rollers 444. Each traction belt 442 provides a continuous loop and is supported on the interior wall of body 450 by the set of rollers 444. In particular, each roller 444 is rotatably supported by a support pin 445. Ends of each support pin 445 are securely attached to an internal side of a respective side wall as in the embodiment shown in FIG. 5. Alternatively, the support pin can be rotatable with roller 444, and either a separate unit or formed integrally therewith. At least one roller 444 is supported on the interior wall of body 450 adjacent a proximal portion of worm gear 434 and another roller 444 is supported on the interior wall of body 450 adjacent a distal end portion 436 of worm gear 434 such that traction belts 442 extend substantially along the length of worm gear 434. The spacing of rollers 444 and the length of traction belts 442 are chosen to provide proper tension in the traction belt 442 when rotated in a continuous loop. By covering a portion of the substantially transverse grooves 446 of the respective belt, i.e. by surface or wall 459 of body 450, it reduces the chances of debris getting caught in the worm gear 434 as the tissue engaging portion loops a sufficient amount to contact the gear, while still providing sufficient engagement/traction with the organ for movement therein. The treads 442 on each side of the belt protrude through one of the slots 454a. The treads 442 of traction portion 443b can be on a substantially planar surface similar to the FIG. 4A embodiment or can be radiused as shown in FIG. 4C, with the raised edges along the longitudinal edges. This radius reduces sharp corners/edges to provide an even more atraumatic surface. The concavity or indentation along the central portion also can accommodate the covering wall 459 of the wall of the tubular portion. (The raised longitudinal edges are exposed through the slots 454a, 454b to provide traction).

Figure 6:
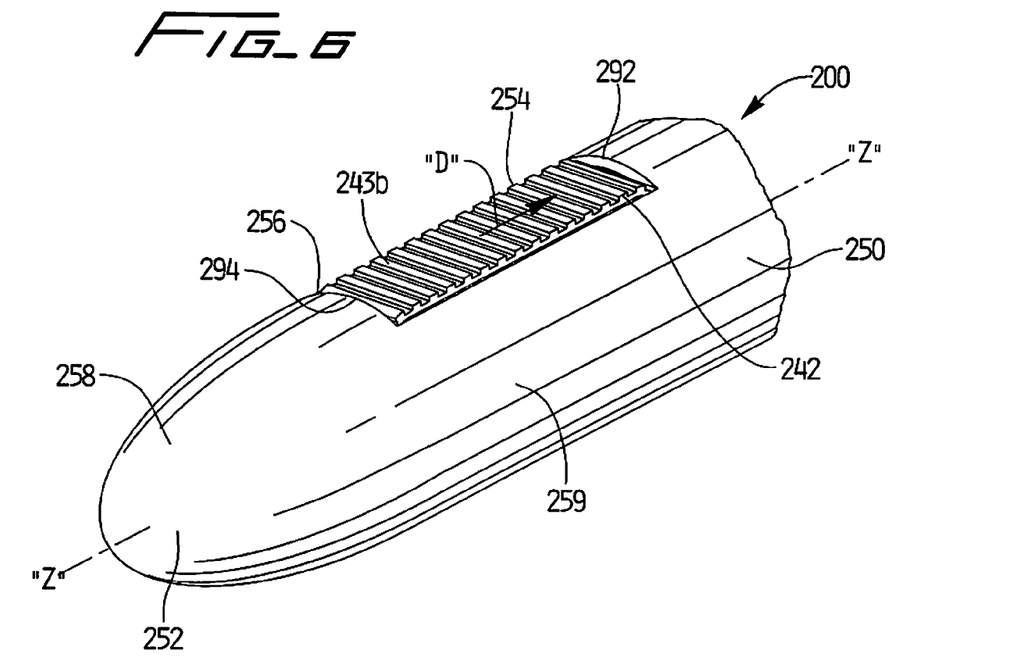
FIG. 6 is perspective view of an endoluminal crawler in accordance with another embodiment of the present disclosure.
Figure 7:
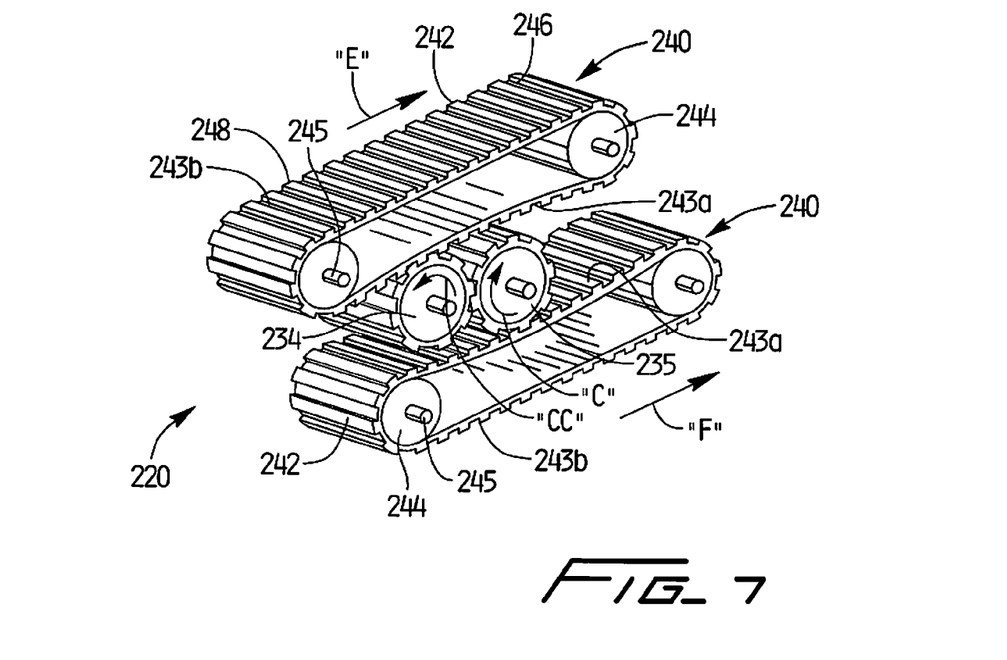
FIG. 7 is a perspective view of an actuation unit of the endoluminal crawler of FIG. 6.

With reference now to FIGS. 6 and 7, an endoluminal device 200 in accordance with another embodiment of the present disclosure is illustrated. Device 200 includes an endoluminal crawler having an outer body 250 defining a longitudinal axis "Z-Z" and an actuation unit 220 accommodated within outer body 250. Endoluminal crawler 200 may be employed as an independent module or as an attachment to a conventional endoscopic apparatus. Outer body 250 is similar to outer body 150 of endoluminal crawler 100 of FIGS. 3 and 4. In particular, outer body 250 includes a tubular portion 256 and a tapered portion 258 to facilitate navigation through the tubular organ. Outer body 250 can have a streamlined torpedo-like shape as shown. Tubular portion 256 defines a pair of spaced apart opposing longitudinal slots 254, preferably about 180° degrees apart. While tapered portion 258 may be integrally formed with tubular portion 256, tapered portion 258 may alternatively be attached to tubular portion 256. Tapered portion 256 may include a flexible or resilient material to adjustably navigate through the tubular organ.

Each longitudinal slot 254 accommodates a traction belt 242 which partially protrudes through longitudinal slot 254 to provide traction against the interior wall of the tubular organ. Each traction belt 242 is continuously looped and is selectively made of material that provides enhanced traction against the interior wall of the tubular organ. In contrast, outer body 250 can be made of or coated with a material providing a minimal amount of friction against the interior wall of tubular organ.

With reference now to FIG. 7, actuation unit 220 is illustrated. Actuation unit 220 includes a pair of pinion gears 234, 235 and a pair of traction units 240. Pinion gears 234, 235 are engaged and meshed with each other such that pinion gears 234, 235 rotate in opposite directions "c," "cc." An actuation device, e.g., motor (not shown), may be operatively coupled to one of the pair of pinion gears 234, 245. Each traction unit 240 includes a traction belt 242 and a set of rollers 244. Traction belt 242 is continuously looped and is supported on an interior wall of body 250 by the set of rollers 244. In particular, each roller 244 is rotatably supported by a support pin 245. Ends of each support pin 245 are securely attached to longitudinal side walls 259 defining longitudinal slot 254. Alternatively, as with the embodiment of FIG. 4, the pin and roller can rotate as a unit with the pin being a separate unit or integral.

The set of rollers 244 in each traction unit 240 are arranged along the longitudinal axis "Z-Z," such that traction belts 242 extend substantially along the length of the tubular portion 256 of body 250. The spacing of rollers 244 and the length of the traction belt 242 are chosen to provide proper tension in the traction belt 242. The elasticity of the material used to make the traction belts 242 may also be considered in determining the proper tension of the traction belt 242.

Each of the continuously looped traction belts 242 includes an engaging portion 243a that engages a respective pinion gear 234, 235 and a traction portion 243b that protrudes out of respective longitudinal slot 254 defined in outer body 250 and provides traction against the interior wall of the tubular organ. Because traction belt 242 is continuously looped, engaging portion 243a and traction portion 243b move in opposite directions when the actuation device rotates pinion gears 234, 235. Thus, upon sufficient movement, the tissue engaging portion 243b becomes the gear engaging portion and the gear engaging portion 243a becomes the tissue engaging (traction) portion. The change in direction of travel for endoluminal crawler 200 can be achieved by simply changing the direction of rotation of pinion gears 234, 235 to move the traction belts 242 in the reverse direction.

Each traction belt 242 includes treads 246 having a plurality of protruding ribs 248. The protruding ribs 248 are preferably uniformly arranged along the length of traction belt 242. The protruding ribs 248 are configured to operatively engage and mesh with respective pinion gears 234, 235. As such, rotation of pinion gears 234, 235 causes rotation of continuously looped traction belts 242. The protruding ribs 248 may be integrally formed with traction belt 242. Alternatively, each protruding rib 248 may be formed on a link and each link may be connected to form a continuously looped traction chain. While traction belt 242 has treads 246 including the plurality of protruding ribs 248, traction belt 242 may define a plurality of substantially transverse grooves configured to mesh with teeth provided on pinion gears 234, 235, as shown and described above in the previous embodiment.

It is also contemplated that a width of traction belt 242 is larger than that of longitudinal slot 254 and the plurality of protruding ribs 248 are dimensioned to fit within longitudinal slot 254. As such, traction belt 242 is rotated within the interior wall of body 250 while the protruding ribs 248 protrude from traction belt 242 through longitudinal slot 254 and provide traction against the interior wall of the tubular organ, e.g. bowel or other part of the body. Such arrangement provides greater stability as traction belt 242 provides support against the interior wall of body 250. It is further contemplated that additional rollers 244 may be provided to direct traction belt 242 away from proximal and distal edges 292, 294 of longitudinal slot 254 to prevent the plurality of protruding ribs 248 from interfering with proximal and distal edges 292, 294. Moreover, longitudinal slot 254 is dimensioned to minimize respective gaps between traction belt 242 and proximal and distal edges 292, 294 of longitudinal slot 254, to prevent pinching of the tubular organ.

The longitudinal slots 254, in some embodiments, can be divided by a wall of the tubular body as in the embodiment of FIG. 4B to reduce debris.

With continued reference to FIG. 7, a single actuation unit 220 having two traction units 240 is illustrated. Endoluminal crawler 200, however, may employ a plurality of actuation units 220 within body 250 to improve traction against the interior wall of tubular organ. In such a case, actuation units 220 are arranged in tandem along the length of body 250. In order to provide uniform traction, actuation units 220 may be uniformly arranged around radial perimeter of body 250. For example, a pair of actuation units 220 may be arranged such that traction portions 243b of traction unit 240 are orthogonal to each other. In any case, the number of actuation units 220 in body 250 may be chosen based on the surgical procedure being performed, as the type of surgical tool that must be carried by endoluminal crawler 200 determines how much traction force is required against the interior walls of tubular organ for propulsion of crawler 200.

As in device 100 and 400, a camera or illuminator can be attached to the (distal) portion of crawler 200 (or to the other crawler devices disclosed herein) for visualization as advanced.

Figures 8, 9:
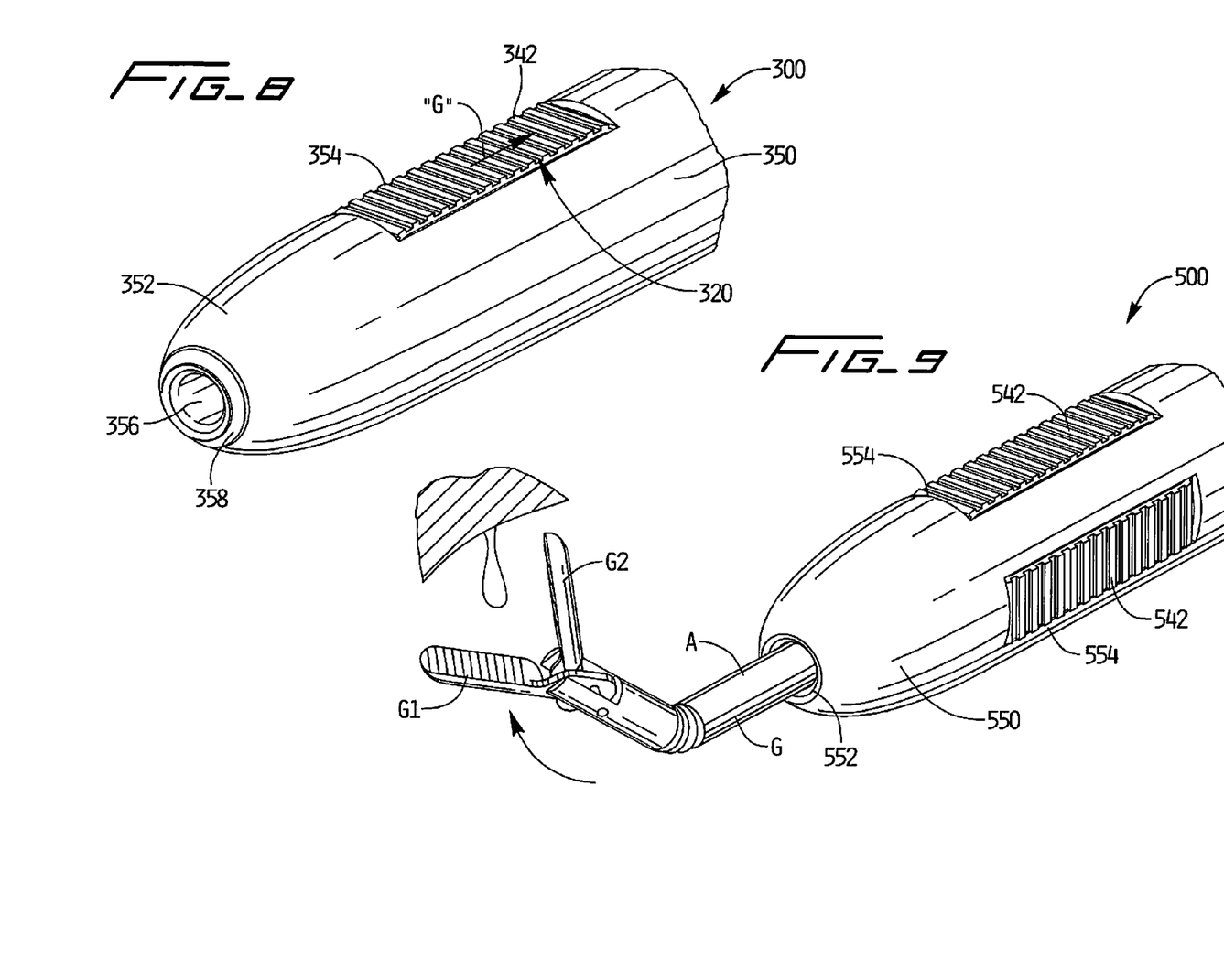
FIG. 8 is a perspective view of an endoluminal crawler in accordance with still another embodiment of the present disclosure.
FIG. 9 is a perspective view of endoluminal crawler in accordance with still another embodiment of the present disclosure.

In the alternate embodiment of FIG. 9, crawler 500 has an opening 552 in body 550 through which surgical instruments can be advanced; e.g. grasper G with movable jaws G1, G2. In this embodiment, the actuation unit can be similar to that of FIG. 4, with traction belts 542 extending through longitudinal slots 554, and movable in a continuous loop by a worm gear (not shown) similar to gear 134 of FIG. 4. The worm gear drive shaft would have an opening extending longitudinally therethrough to accommodate the shaft A of grasper G. Jaws G1, G2 would be advanced through the drive shaft opening in a closed position and remotely operable (e.g. opening/closing and articulation).

With reference to FIG. 8, an endoluminal device 300 in accordance with another embodiment of the present disclosure is illustrated. Endoluminal device 300 includes a crawler having an outer body 350 and an actuation unit (not shown) accommodated within outer body 350. Any of the above described actuation units may be employed in endoluminal crawler 300 to move traction belt 342. Moreover, endoluminal crawler 300 may be employed as an independent module or an attachment to a conventional endoscope, as described above. Outer body 350 of endoluminal crawler 300 has a generally tubular configuration with a tapered distal portion 352. The non-tapered portion of outer body 350 defines a pair of opposing longitudinal slots 354, preferably about 180° degrees apart although others spacings and additional slots to accommodate additional belts are contemplated. Each longitudinal slot 354 accommodates a continuously looped traction belt 342 which partially protrudes through longitudinal slot 354 to provide traction against the interior wall of the tubular organ. Traction belts 342 can be similar to belts 242 or 142 of the embodiments described above and driven in a similar fashion. Traction belts 342 can also be similar to belts 442 with body 350 and slots 354 similar to body 450 and slots 454a, 454b of FIG. 4B.

Body 350 defines at a distal end portion thereof an aperture 356 and a viewing window 358 radially surrounding aperture 356. Aperture 356 is in communication with an integral working channel that extends along the length of body 350. The integral working channel is provided for the passage of the instruments and/or water into the tubular organ through aperture 356. The channel in some embodiments can be formed in the drive shaft (not shown) which rotates the gears as in the embodiment of FIG. 4C. Viewing window 358 is made of a transparent material so that a camera and light source provided within body 350 adjacent viewing window 358 may capture images of the surgical site through viewing window 358 and relay the images to an external display terminal for viewing by the user. Optionally, body 350 may provide a separate channel (e.g. built into the wall of body portion 350) for the camera and the light source to provide fluid tight environment for the camera and the light source. It is further contemplated that body 350 may further include a power supply to provide power to the actuation unit.

As noted above, endoluminal crawler 100, 200, 300, 400, 500 may be employed as an independent module as well as an attachment to a conventional endoscope. Operation of either type is substantially similar and will be described together in the interest of brevity. For brevity, only endoluminal crawler 100 will be described as the other crawlers described herein operate in a similar manner. In operation, crawler 100, if separate, is first attached to a distal end portion of an insertion tube of a conventional endoscope. If endoluminal crawler 100 is an independent module it may attach thereto other surgical tools to guide the surgical tools to a surgical site of interest. Once the initial preparation has been performed, endoluminal crawler 100 is inserted through a tubular organ, at which time traction portions 143b of belts 142 are in contact with the interior walls of the tubular organ. Thereafter, a user powers on actuation device 130 of actuation unit 120 which in turn rotates worm gear 134. Actuation can be achieved remotely or via electrical connections extending from the actuation unit 120 connected to an external power switch. Upon actuation, traction belts 142 engaging worm gear 134 rotate on a continuous loop. As such, traction portions 143b move in the direction of arrows "A" and "B" as shown in FIG. 3. Traction portions 143b of traction belts 142 propel endoluminal crawler 100 distally in the direction opposite of arrows "A," "B." Devices 200, 300, 400 and 500 would also operate by powering on their respective actuation devices to move their respective traction belts.

As endoluminal crawler 100 travels into the tubular organ, the insertion tube or surgical tools attached to endoluminal crawler 100 follows into the tubular organ. Once endoluminal crawler 100 is in position along the tubular organ, as determined by a user who views the images of the tubular organ on an external display terminal, the surgical tools attached to endoluminal crawler 100 or inserted through the endoscope can be placed at the proper surgical site. At this time, various procedure(s) including, e.g., removal of polyps, irrigation, suction, and/or biopsy, may be performed by the surgical tools passed through working channel 136. Upon completion of the surgical procedure(s), endoluminal crawler may be removed by reversing the direction of rotation of actuation device 130 which in turn moves the traction portions 143b in the direction opposite of arrows "A," "B," thereby propelling crawler 100 in a proximal direction of arrows "A" and "B."

Self-propelled endoluminal crawler 100 navigates through the tubular organ with ease as compared to the manual insertion of the tubular member of the endoscope. In addition, the self-propelled endoluminal crawler 100 reduces patient discomfort and trauma caused by excessive extension or dilation of the tubular member which can take place during manual insertion of the endoscope into the tubular member.

The traction belts of the crawler devices 100, 200, 300, 400 and 500 described herein can also be driven by a rotating shaft, powered by an external drive motor or device. The devices can also have a wire connection to an external power source.

FIG. 10 show crawler device 100' mounted to flexible tube 630 of endoscope 610. Crawler device 100' is identical to device 100, except for the mounting to the endoscope tube, and therefore identical parts to crawler 100 are labeled with "prime" designations, e.g. body 150' and belt 142'. Endoscope 610 is identical to endoscope 10 except it includes the crawler device 100'. The identical parts to endoscope 10 are labeled in the "600" series and therefore for brevity are not discussed herein as the discussion of the components of endoscope 10 above are applicable to endoscope 610.

It will be understood that various modifications may be made to the embodiments of the presently disclosed endoluminal crawler. Therefore, the above description should not be construed as limiting, but merely as exemplifications of embodiments. Those skilled in the art will envision other modifications within the scope and spirit of the present disclosure.

What is claimed is:

1. A self-propelled surgical endoluminal device comprising:
   a body including a tubular portion defining first and second slots, and a wall interposed between the first and second slots, the wall including an inner surface and an outer surface; and
   an actuation unit disposed within the body, the actuation unit including:
      an actuator providing a rotational output; and
      a fraction belt including first and second traction portions and an engaging portion interposed between the first and second traction portions, the first and second traction portions at least partially protruding out of the first and second slots, respectively, the engaging portion in registration with the inner surface of the wall of the body, the outer surface of the wall of body configured to slidably engage tissue, at least a portion of the engaging portion operatively engaging the actuator,
   wherein the first and second traction portions and the engaging portion are integrally formed.

2. The self-propelled endoluminal device according to claim 1, further comprising at least one roller rotatably supporting the traction belt in the body, wherein the traction belt is continuously looped such that the rotational output of the actuator provides continuous rotation of the traction belt.

3. The self-propelled endoluminal device according to claim 2, wherein the actuation unit further includes a worm gear defining a longitudinal axis, the worm gear being operatively coupled to the actuator and engaging the engaging portion of the traction belt.

4. The self-propelled endoluminal device according to claim 3, wherein the worm gear defines a working channel extending along a length of the worm gear, and a distal end portion of the body defines an aperture, the working channel and the aperture configured to receive a surgical tool therethrough.

5. The self-propelled endoluminal device according to claim 2, wherein the actuation unit further includes at least one pinion gear, the at least one pinion gear being operatively coupled to the actuator and engaging the engaging portion of the traction belt such that the rotational output of the actuator rotates the continuously looped traction belt.

6. The self-propelled endoluminal device according to claim 1, wherein the body includes a tapered portion extending longitudinally from the tubular portion.

7. The self-propelled endoluminal device according to claim 6, wherein the tapered portion includes a flexible material configured to conform to a shape of a tubular organ.

8. The self-propelled endoluminal device according to claim 1, wherein the body defines a working channel extending along the length of the body, and a distal end portion of the body defines an aperture, the aperture and the working channel configured to receive a surgical tool therethrough.

9. The self-propelled endoluminal device according to claim 8, wherein the body includes a viewing window radially surrounding the aperture.

10. The self-propelled endoluminal device according to claim 1, further comprising an internal power source to supply power to the actuator providing the rotational output.

11. The self-propelled endoluminal device according to claim 10, further comprising a light source, the light source being powered by the internal power source.

12. The self-propelled endoluminal device according to claim 1, wherein the first and second traction portions are disposed on opposing sides of the traction belt with respect to a length of the traction belt.

13. An endoscope apparatus comprising:
   a housing;
   a flexible tube longitudinally extending from the housing; and
   an endoluminal device attached to the flexible tube, the endoluminal device including:
      a body including a tubular portion defining first and second slots, and a wall interposed between the first and second slots, the wall including an inner surface and an outer surface; and
      an actuation unit disposed within the body, the actuation unit including:
         an actuator providing a rotational output; and
         a fraction belt including first and second traction portions disposed on opposing sides of the traction belt with respect to a length of the traction belt, and an engaging portion interposed between the first and second traction portions, the first and second traction portions partially protruding out of the first and second slots of the body, respectively, the engaging portion operatively engaging the actuator, at least a portion of the engaging portion in registration with the inner surface of the wall of the body, the outer surface of the wall of the body configured to slidably engage tissue, wherein the first and second traction portions and the engaging portion are integrally formed.

14. The endoscope apparatus according to claim 13, further comprising at least one roller rotatably supporting the traction belt in the body, wherein the traction belt is continuously looped such that the rotational output of the actuator provides continuous rotation of the traction belt.

15. The endoscope apparatus according to claim 14, wherein the actuation unit further includes at least one pinion gear operatively engaging the actuator and the engaging portion of the traction belt such that the rotational output of the actuator rotates the continuously looped traction belt.

16. The endoscope apparatus according to claim 13, wherein the housing defines an aperture configured to receive a surgical tool therethrough, and the body defines an opening at a distal portion thereof, the opening configured to receive the surgical tool therethrough.

17. The endoscope apparatus according to claim 13, wherein the actuation unit further includes a worm gear defining a longitudinal axis, the worm gear being operatively coupled to the actuator and engaging the engaging portion of the traction belt.

18. The endoscope apparatus according to claim 17, wherein the worm gear defines a working channel therein, the working channel extending along a length of the worm gear.

19. The endoscope apparatus according to claim 13, further comprising a camera in the body.

20. The endoscope apparatus according to claim 13, wherein the body includes a tapered portion including a flexible material configured to conform to a shape of a tubular organ.

* * * * *